United States Patent [19]

Kuroda et al.

[11] Patent Number: 4,828,720
[45] Date of Patent: May 9, 1989

[54] LIQUID SEPARATING AGENT AND LIQUID SEPARATING METHOD

[75] Inventors: Katsuhiko Kuroda, Yokohama; Hideki Yamanouchi, Machida, both of Japan

[73] Assignee: Mitsubishi Chemical Industries Limited, Tokyo, Japan

[21] Appl. No.: 13,340

[22] Filed: Feb. 11, 1987

[30] Foreign Application Priority Data

Feb. 25, 1986 [JP] Japan ................................. 61-39736
Feb. 26, 1986 [JP] Japan ................................. 61-40898
Feb. 27, 1986 [JP] Japan ................................. 61-42483

[51] Int. Cl.$^4$ ...................... B01D 33/00; B01D 21/26
[52] U.S. Cl. ..................................... 210/782; 210/516; 210/789; 252/60; 422/101; 422/102; 436/177; 494/37
[58] Field of Search .................. 252/60; 210/781, 782, 210/787, 789, 516, 514; 549/364, 365; 494/37; 422/101, 102; 436/177, 178

[56] References Cited

U.S. PATENT DOCUMENTS

| | | | |
|---|---|---|---|
| 4,131,612 | 12/1978 | Uchiyama | 549/364 |
| 4,172,803 | 10/1979 | Ichikawa et al. | 252/60 |
| 4,310,430 | 1/1981 | Ichikawa et al. | 210/782 |
| 4,426,290 | 1/1984 | Ichikawa et al. | 210/782 |
| 4,770,779 | 9/1988 | Ichikawa et al. | 210/789 |

FOREIGN PATENT DOCUMENTS

| | | | |
|---|---|---|---|
| 56-4053 | 1/1981 | Japan | 210/782 |
| 58-53759 | 3/1983 | Japan | 210/782 |
| 58-37560 | 3/1983 | Japan . | |

OTHER PUBLICATIONS

Die Makromolekulare Chemie, vol. 154, 1972, pp. 317-319, Basel, CH; D.C. Phillips et al. "Copolymerization of Styrene and Diethyl Furmarate with Zinc Bromide, Part I. Electroinitiation".

Primary Examiner—W. Gary Jones
Attorney, Agent, or Firm—Oblon, Fisher, Spivak, McClelland & Maier

[57] ABSTRACT

A liquid separating agent consisting essentially of (A) a separating layer-forming material which is a polymeric oily substance selected from the group consisting of a copolymer of an α-olefin with an α,β-unsaturated dicarboxylic acid diester and a copolymer of a styrene with an α,β unsaturated dicarboxylic acid diester and (B) an organic gelling agent which is a condensation product of a benzaldehyde with a tetra- or higher hydric alcohol.

7 Claims, No Drawings

LIQUID SEPARATING AGENT AND LIQUID SEPARATING METHOD

The present invention relates to a liquid separating agent and a liquid separating method. More particularly, the present invention relates to a liquid separating agent useful for separating a specific component such as blood serum or blood plasma and another component in a liquid sample such as blood by utilizing the difference between their specific gravities, which has a specific gravity falling inbetween the specific gravities of the two components and which is capable of forming a partition wall between the two components to facilitate the separation of the two components, and a liquid separating method by means of such an agent.

For the separation of a specific component and another component in a liquid sample by utilizing the difference between their specific gravities, as in the case of the separation of blood serum or blood plasma, it is known to use a liquid separating agent which facilitates the separation of the two components by forming a partition wall between them. As such a liquid separating agent, it is known to use a highly viscous oil such as a silicone oil, a chlorinated polybutene oil or a copolymer of an α-olefin with a maleic acid diester, as a separating layer-forming material, in combination with a fine inorganic powder such as hydrophobic fine powder silica or hydrophobic smectites clay, as a thixotropic agent, so as to form a gel having thixotropic properties, which exhibits fluidity during centrifugal separation, but remains to be non-flowable at any other time.

However, such a conventional liquid separating agent is essentially of non-uniform system, since an insoluble inorganic fine powder is used as a thixotropic agent, as dispersed in the separating layer-forming material. Therefore, phase separation as between the separating layer-forming material and the thixotropic gent is likely to result under a condition of heat treatment or during storage for a long period of time or under a condition of centrifugal separation, and there have been drawbacks such that the function of the partition wall deteriorates due to the change of the physical properties of the gel, and the separated component is likely to be contaminated by the separation of the oil content.

Accordingly, it is an object of the present invention to provide a practically excellent liquid separating agent and liquid separating method free from the above-mentioned drawbacks.

In the broadest sense, the present invention provides a liquid separating agent consisting essentially of (A) a separating layer-forming material and (B) an organic gelling agent, and a method for separating a specific component and another component in a liquid sample by utilizing the difference between their specific gravities and by forming, between the two components, a partition wall of a material having a specific gravity falling inbetween the specific gravities of the two components, which comprises centrifuging, in a liquid separator, said liquid sample together with an effective amount of a liquid separating composition consisting essentially of (A) a separating layer-forming material and (B) an organic gelling agent, until said composition forms a continuous partition wall at the interface between the specific component and another component.

Now, the present invention will be described in detail with reference to the preferred embodiments.

The liquid separating agent of the present invention is a composition consisting essentially of a separating layer-forming material and an organic gelling agent.

As the separating layer-forming material, various organic liquids may be employed so long as their specific gravities fall inbetween the specific gravities of the two components in the liquid to be separated. Namely, it ranges from various organic solvents or plasticizers having low viscosities to polymeric oily substances having high viscosities. From the practical point of view, a polymeric oily substance preferably having a viscosity within a range of 200 to 600,000 cPs at a temperature of 25° C., is suitable in that it is stable and presents proper fluidity and gelling properties. Such a polymeric oily substance includes, for example, a silicone, a chlorinated polybutene, a chlorinated polystyrene, a polyacrylate, a polymethacrylate, and a copolymer of an α-olefin or a styrene with an α,β-unsaturated dicarboxylic acid diester.

Among the above-mentioned separating layer-forming materials, a copolymer of an α-olefin or a styrene with an α, β-unsaturated dicarboxylic acid diester is preferred. Particularly suitable among them is a copolymer of a styrene with an α,β-unsaturated dicarboxylic acid diester having the formula:

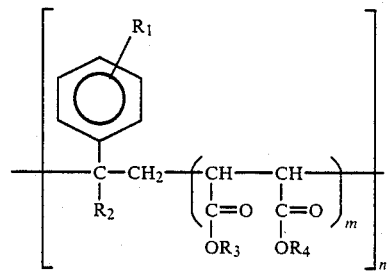

wherein each of $R_1$ and $R_2$ is a hydrogen atom or an alkyl group having from 1 to 3 carbon atoms, each of $R_3$ and $R_4$ is an alkyl group having from 1 to 18 carbon atoms or an aryl group, m is from 0.2 to 5.0, an n is from 3 to 200.

As compared with liquid separating agents composed mainly of a silicone oil, such a copolymer is superior in that water repellent staining on the inner wall of the separator or the degradation during the sterilizing step by ionizing radiation is minimum, and it is less expensive and economically advantageous as a common disposal product.

Further, as compared with a liquid separating agent composed mainly of a chlorinated polybutene oil or a copolymer of an α-olefin with a maleic acid diester, the affinity with an organic gelling agent is better, and phase separation hardly takes place under a condition of heat treatment or during storage for a long period of time or under a condition of centrifugal separation. The deterioration of the function of the partition wall due to the change in the physical properties of the gel or the contamination of a separated component due to the separation of an oil content, is scarcely brought about. Further, it has adequate heat resistance, whereby the formation of decomposition products during the preparation, filing or sterilizing steps, or the consequential contamination of the separated omponent, is scarcely brought about.

The separating layer-forming material is suitably selected so that it has a suitable viscosity and specific gravity depending upon the viscosity of the liquid to be separated or upon the specific gravities of the two components in the liquid and the difference in the specific gravities of the two components. For instance, in the case of the copolymer of a styrene with an $\alpha,\beta$-unsaturated dicarboxylic acid diester having the above formula, the specific gravity can be adjusted by controlling the carbon numbers of the hydrocarbon groups $R_3$ and $R_4$ and by controlling the copolymerization molar ratio m. In general, the specific gravity can be increased by reducing the total carbon number of R and $R_4$ or by increasing the copolymerization ratio m. Further, the viscosity can be adjusted most effectively by controlling the polymerization degree n. More specifically, for the preparation of a separating layer-forming material having a controlled viscosity and specific gravity, the copolymerization ratio m can be adjusted by selecting the carbon numbers of the hydrocarbon groups $R_3$ and $R_4$ of the a,8-unsaturated dicarboxylic acid diester used for the copolymerization reaction of the styrene with the $\alpha,\beta$-unsaturated dicarboxylic acid diester, or by selecting the molar ratio of the starting materials, and the polymerization degree n can be adjusted by adjusting the polymerization temperature or by the selection of the polymerization solvent, or by the use of a radical transfer agent, whereby it is possible to readily obtain a separating layer-forming material having a predetermined viscosity and specific gravity.

For the separation of blood serum, the specific gravity at 25° C. is within a range of from 1.00 to 1.08, preferably from 1.03 to 1.06, and the viscosity at 25° C. is within a range of from 1,000 to 1,500,000 cPs, preferably from 10,000 to 600,000 cPs.

The organic gelling agent to be used for the liquid separating agent of the present invention includes, for example, a condensation product of a benzaldehyde with a tetra- or higher hydric alcohol, a nitrohumic acid adduct of a water-soluble protein, hydrogenated castor oil and 12-hydroxy stearic acid.

The benzaldehyde to be used for the above condensation product may be benzaldehyde or benzaldehyde having on its aromatic ring at least one substituent, for example, an alkyl group such as methyl, ethyl, propyl, isopropyl or tert-butyl, an alkoxy group such as methoxy or ethoxy, a hydroxyl group, or a halogen atom. More specifically, the benzaldehyde includes tolualdehyde, cinnamaldehyde, cuminaldehyde, methoxybenzaldehyde, piperonal, chlorobenzaldehyde and p-oxy-m-methoxybenzaldehyde.

The tetra- or higher hydric alcohol may be sorbitol, xylitol, pentaerythritol or mannitol. Their derivatives having substituents which do not adversely affect the condensation reaction with the aldehyde, may also be employed. Usually, however, sorbitol, xylitol or pentaerythritol, particularly a penta- or higher hydric alcohol such as sorbitol or xylitol, is preferably employed. Further, substantially the same results can be obtained when a part of the tetra- or higher hydric alcohol is substituted by saccharides such as glucose, galactose, mannose, fructose, malt sugar, lactose, sucrose, and dextrin. More specifically, the condensation product of a benzaldehyde with a tetra- or higher hydric alcohol includes dibenzylidene sorbitol, tribenzylidene sorbitol or a alkyl-substituted dibenzylidene sorbitol. Among them, a condensation product of sorbitol with benzaldehyde is particularly preferred because it has excellent gelling properties.

Thus, the liquid separation can most effectively be conducted when a copolymer of a styrene with an $\alpha,\beta$-unsaturated dicarboxylic acid diester as the separating layer-forming material and a condensation product of sorbitol with benzaldehyde as the thixotropic agent are employed.

The liquid separating agent of the present invention is prepared by dispersing the above-mentioned organic gelling agent in the above-mentioned separating layer-forming material to provide proper thixotropic properties. The composition thus obtained forms a gel which exhibits fluidity when a stress such as a centrifugal force is exerted thereto and which shows a stabilized non-fluidity under a usual condition, and thus is suitably employed for liquid separation.

More specifically, the liquid separating agent can be readily obtained by heating the separating layer-forming material at a temperature within a range of from 100 to 200° C., adding a predetermined amount of the organic gelling agent, and stirring the mixture under heating for from 1 to 5 hours until the gelling agent is uniformly dissolved. When used as a separating agent for blood serum, the above liquid separating agent is poured into a blood collecting tube while it is still hot, and then cooled to form a gel. Thus, it can be used quite simply.

The amount of the organic gelling agent relative to the separating layer-forming material varies depending upon the polarity and the viscosity of the separating layer-forming material. Generally, the higher the polarity or the lower the viscosity, the larger the amount required. However, it is usually within a range of from 0.02 to 5 parts by weight, preferably from 0.1 to 1 part by weight, relative to 100 parts by weight of the separating layer-forming material.

If the amount of the organic gelling agent is too small, the strength of the gel during the liquid separation will be inadequate, and the partition wall tends to flow out, whereby no adequate function will be obtained. On the other hand, if the amount is excessive, the fluidity will be inadequate, and the transfer properties required for the formation of a partition wall will be poor, whereby no adequate function will be obtained.

The suitable physical properties of the composition constituting the liquid separating agent of the present invention vary depending on the type of the liquid subjected to separation treatment. For example, in a case where the liquid separating agent is used as a separating agent for blood serum or blood plasma, its specific gravity should suitably be at an intermediate level between the serum or plasma and blood cells, i.e. from 1.035 to 1.060, at a temperature of 25° C., and its viscosity should suitably be within a range of from 200,000 to 2,000,000 cPs at 25° C.

Further, in order to precisely control the viscosity and specific gravity, fine inorganic powder such as silica, bentonite or titanium oxide, may be used. The amount varies depending upon the desired viscosity and specific gravity. However, it is usually not higher than 1 part by weight relative to 100 parts by weight of the separating layer-forming material. In the liquid separating method of the present invention, the liquid separating operation itself may be conducted in accordance with a conventional method for separating a specific component and another component in a liquid sample by utilizing the difference between their specific gravities and by forming, between the two components, a partition wall of a material having a specific gravity falling inbetween the specific gravities of the two components. According to the present invention, the liquid separation is conducted by centrifuging, in a liquid separator, the liquid sample together with an effective amount of a liquid separating composition consisting essentially of (A) a separating layer-forming material and (B) an organic gelling agent, until the composition forms a continuous partition wall at the interface between the specific component and another component.

The liquid separating agent of the present invention forms a colorless transparent completely uniform system, which is totally different in its nature from the conventional liquid separating agents treated with an insoluble thixotropic agent such as fine inorganic powder, which form an opaque non-uniform system. The liquid separating agent of the present invention has extremely useful properties from the practical point of view.

Namely, since the liquid separating agent of the present invention forms a uniform system, it is free from an undesirable phase separation phenomenon as between the separating layer-forming material and the thixotropic agent during the heat treatment or storage for a long period of time, or during the centrifugal separation, and there will be no decrease in the function of the partition wall, or no stains due to the separation of an oil component. Further, from the viewpoint of production, the liquid separating agent of the present invention is advantageous in that it can readily be prepared by simple heating and dissolving operation, and the production cost will be very inexpensive, while the conventional liquid separating agents employing an insoluble fine powder thixotropic agent, require inefficient dispersion and kneading steps by means of e.g. a three-roll mill or a kneader. Furthermore, in the treatment of the used liquid separating agent, no trouble due to the formation of ash content or due to the generation of hydrogen chloride gas, and the used agent can readily be incinerated.

Particularly when a copolymer of a styrene with an α,β-unsaturated dicarboxylic acid diester is used as the separating layer-forming material, it has a high affinity with the organic gelling agent as the thixotropic agent, and the resulting liquid separating agent has high heat resistance. Thus, the liquid separating agent has extremely useful properties from the practical viewpoint, without any troubles such as contamination of the separated component with an oil content due to phase separation, or contamination of the separated component with thermal decomposition products.

In a case where a condensation product of sorbitol with benzaldehyde is used as the organic gelling agent in the liquid separating agent of the present invention, the gelling power is high, and it is possible to impart the necessary gelling properties to the separating layer-forming material with a relatively small amount. Further, the condensation product is chemically neutral and hydrophobic, and has excellent heat resistance.

When a copolymer of a styrene with an c,8-unsaturated dicarboxylic acid diester is used as the separating layer-forming material and a condensation product of sorbitol with benzaldehyde is used as the organic gelling agent, the mutual affinity to each other is quite high, and the heat resistance can be made high.

Thus, according to the liquid separating method of the present invention, there will be no trouble of phase separation as between the separating layer-forming material and the thixotropic agent even under a condition for centrifugal separation, and there will be no decrease in the function of the partition wall, or no contamination due to the separation of the oil content, whereby it is possible to obtain excellent liquid separating effects.

Particularly when a liquid separating agent wherein a copolymer of a styrene with an α,β-unsaturated dicarboxylic acid diester is used as the separating layer-forming material, is employed, extremely useful practical liquid separation properties can be obtained without troubles such as contamination of the separated component with an oil content due to phase separation or contamination of the separated component with thermal decomposition products.

Now, the present invention will be described in further detail with reference to Examples. However, it should be understood that the present invention is by no means restricted by these specific Examples.

EXAMPLE 1

(Preparation of a copolymer)

Into a 1 liter four-necked flask, 228 g (1 mol) of dibutyl maleate was charged and heated to 160° C. under a nitrogen stream. Then, a mixture comprising 104 g (1 mol) of styrene and 8.76 g (0.06 mol) of di-tert-butyl peroxide, was continuously dropwise added thereto under stirring over a period of 5 hours. After the addition, the mixture was further reacted at the same temperature for 1 hour. After the completion of the reaction, low boiling point components and unreacted monomers contained in the reaction mixture were removed by distillation under a reduced pressure of from 1 to 3 mmHg, to obtain 309 g (yield: 93%) of a styrene-dibutyl maleate copolymer.

The copolymer thus obtained was a colorless transparent liquid having a viscosity of 30,000 cPs and a specific gravity of 1.058 at 25° C.

EXAMPLE 2

(Preparation of a copolymer)

The reaction was conducted in the same manner as in Example 1 except that 1 mol of the dibutyl maleate was changed to 160 g (0.7 mol) of dibutyl fumarate and 102 g (0.3 mol) of di-2-ethylhexyl fumarate, whereby 329 g (yield: 99%) of a styrene-fumaric acid diester copolymer was obtained. The copolymer thus obtained was a colorless transparent liquid having a viscosity of 90,000 cPs and a specific gravity of 1.042 at 25° C.

EXAMPLES 3 to 5

(Preparation of colpolymers)

By using α,β-unsaturated dicarboxylic acid diesters shown in Table 1, polymerization was conducted in the same manner as in Example 1 except that the reaction conditions were as shown in Table 1. The properties of the copolymers thus obtained are shown in Table 1 together with the results of Examples 1 and 2.

TABLE 1

| Example | 1 | 2 | 3 | 4 | 5 |
|---|---|---|---|---|---|
| Diesters* (charged mols) | | | | | |
| DBM | 1.0 | | | | |
| DBF | | 0.7 | 1.0 | | 0.5 |
| DOF | | 0.3 | | 1.0 | 0.5 |

TABLE 1-continued

| Example | 1 | 2 | 3 | 4 | 5 |
|---|---|---|---|---|---|
| Viscosity (cPs, 25° C.) | 30,000 | 90,000 | 1,300,000 | 27,000 | 50,000 |
| Specific gravity ($d_4^{25}$) | 1.058 | 1.042 | 1.069 | 1.000 | 1.026 |

*Abbreviations of diesters:
DBM: Dibutyl maleate
DBF: Dibutyl fumarate
DOF: Di-2-ethylhexyl fumarate

EXAMPLES 6

(Preparation of liquid separating agents)

Into a four-necked flask, the separating layer-forming material and the thixotropic agent were charged in the proportions as identified in Table 2, and the mixture was heated to 190° C. and stirred for 2 hours to dissolve the thixotropic agent, and then cooled to obtain a liquid separating agent in the form of a gel having thixotropic properties. The physical properties are also shown in Table 2.

TABLE 2

| | (Proportions being by weight) | | |
|---|---|---|---|
| Composition Nos. | 1 | 2 | 3 |
| Copolymer prepared in Example 1 | 100 | | |
| Copolymer prepared in Example 2 | | 100 | |
| Styrene-di-n-hexyl fumarate copolymer *1 | | | 100 |
| Gelol D *2 | 0.35 | 0.35 | 0.35 |
| Specific gravity ($d_4^{25}$) | 1.058 | 1.042 | 1.045 |
| Viscosity (cPs, 25° C.) | 300,000 | 600,000 | 200,000 |

*1 Copolymer of styrene with di-n-hexyl fumarate, specific gravity $d_4^{25}$: 1.045, viscosity: 90,000 cPs (25° C.).
*2 Condensation product of sorbitol with benzaldehyde, manufactured by Shin Nihon Rika K.K.

EXAMPLE 7

(Preparation of liquid separating agents)

Into a four-necked flask, the separating layer-forming material and the organic gelling agent were charged in the proportions as identified in Table 3, and the mixture was heated to 190° C. and stirred for 2 hours to dissolve the organic gelling agent, and then cooled to obtain a liquid separating agent in the form of a gel having thixotropic properties. The physical properties are also shown in Table 3.

TABLE 3

| Composition Nos. | 4 | 5 |
|---|---|---|
| α-olefin-dimethyl maleate copolymer *1 | 100 | |
| Chlorinated polybutadiene *2 | | 100 |
| Gelol D *3 | 0.5 | 0.5 |
| Specific gravity ($d_4^{25}$) | 1.050 | 1.052 |
| Viscosity (cPs, 25° C.) | 500,000 | 600,000 |

*1 Copolymer of a mixture of α-olefins having 12 and 14 carbon atoms with dimethyl maleate, specific gravity $d_4^{25}$: 1.050, viscosity: 80,000 cPs (25° C.).
*2 Chlorine adduct of polybutene, specific gravity $d_4^{25}$: 1.052, viscosity 100,000 cPs (25° C.).
*3 Condensation product of sorbitol with benzaldehyde, manufactured by Shin Nihon Rika K.K.

EXAMPLE 8

(Evaluation: Blood serum separation test)

Into a Spitz's tube, 2 cc of one of the liquid separating agents prepared in Examples 6 and 7 and collected total blood sample were introduced, and left to stand still. The blood coagulation proceeded. After the blood sample underwent separation into blood serum and blood clot, it was subjected to centrifugal separation at a rotational speed of 3,000 rpm for 10 minutes. With each of the liquid separating agents of Examples 6 and 7, a gel of the liquid separating agent formed inbetween the blood serum and the blood clot. The blood serum was readily taken out from the Spitz's tube by decantation. EXAMPLE 9 (Evaluation: Stability)

By means of a three-roll mill, 100 parts by weight of silicone oil (specific gravity $d_4^{25}$: 0.992, viscosity 100 Ps (25° C.)) and 3 parts by weight of fine powder of hydrophobic silica (Aerozil R-972, manufactured by Nihon Aerozil Company) were thoroughly kneaded to obtain a gel having thixotropic properties.

Into Spitz's tubes, this gel (Comparative Example) and the liquid separating agents prepared in Examples 6 and 7, were introduced, respectively, and kept at 40° C. for 1 week to examine the stability of the respective gels. The results are shown nn Table 4.

TABLE 4

| | Separating agents | Stability* |
|---|---|---|
| Example | Composition No. 1 | O |
| | Composition No. 2 | O |
| | Composition No. 3 | O |
| | Composition No. 4 | O |
| | Composition No. 5 | O |
| Comparative Example | Silicone oil/silica | Δ |

*Evaluation standards for stability:
O: No separation
Δ: Separation of oil content observed
X: Phase separation observed

We claim:

1. A method for separating a specific component and another component in a blood sample by utilizing the difference between their specific gravities and by forming, between the two components, a partition wall of a material having a specific gravity falling inbetween the specific gravities of the two components, which comprises centrifuging, in a liquid separator, said blood sample together with an effectve amount of a blood separating composition consisting essentially of (A) a separating layer-forming material which is a polymeric oily substance selected from the group consisting of a copolymer of an α-olefin with an α,β-unsaturated dicarboxylic acid diester and a copolymer of a styrene with an α,β-unsaturated dicarboxylic acid diester and (b) an organic gelling agent which is a condensation product of a benzaldehyde with a tetra- or higher hydric alcohol, until said composition forms a continuous partition wall at the interface between the specific component and another component.

2. The method according to claim 1, wherein the compostition has a specific gravity of from 1.035 to 1.060 and a viscosity of from 1,000 to 1,500,000 cPs at a temperature of 25° C.

3. A blood separating agent consisting essentially of (A) a separating layer-forming material which is a polymeric oily substance selected from the group consisting of a copolymer of an α-olefin with an α,β-unsaturated dicarboxylic acid diester and a copolymer of a styrene with an α,β-unsaturated dicarboxylic acid diester and (B) an organic gelling agent which is a condensation product of a benzaldehyde with a tetra- or higher hydric alcohol.

4. The liquid separating agent according to claim 3, wherein the separating layer-forming material (A) is a copolymer of a styrene with an α,β-unsaturated dicarboxylic acid diester, having a sturcture of the formula:

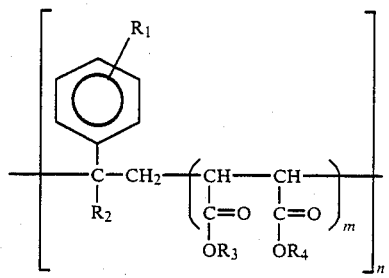

wherein each of $R_1$ and $R_2$ is a hydrogen atom or an alkyl group having from 1 to 3 carbon atoms, each of $R_3$ and $R_4$ is an alkyl group having from 1 to 18 carbon atoms or an aryl group, m is from 0.2 to 5.0, and n is from 3 to 200.

5. The liquid separating agent according to claim 3, wherein the organic gelling agent (B) is a condensation product of benzaldehyde with sorbitol.

6. The liquid separating agent according to claim 3, wherein the organic gelling agent (B) is in an amount of from 0.02 to 5.0% by weight relative to the amount of the separating layer-forming material (A).

7. The liquid separating agent according to claim 3, which has a specific gravity of from 1.035 to 1.060 and a viscosity of from 1,000 to 1,500,000 cPs at a temperature of 25° C.

* * * * *